United States Patent [19]

Grubb

[11] Patent Number: 5,521,166
[45] Date of Patent: May 28, 1996

[54] ANTIPROGESTIN CYCLOPHASIC HORMONAL REGIMEN

[75] Inventor: Gary S. Grubb, Bridgewater, N.J.

[73] Assignee: Ortho Pharmaceitical Corporation, Raritan, N.J.

[21] Appl. No.: 359,159

[22] Filed: Dec. 19, 1994

[51] Int. Cl.⁶ ................................................. A61K 31/56
[52] U.S. Cl. ........................ 514/170; 514/171; 514/179; 514/843; 514/899
[58] Field of Search .................................. 514/170, 171, 514/843, 899, 179

[56] References Cited

U.S. PATENT DOCUMENTS

| | | | |
|---|---|---|---|
| 4,386,085 | 5/1983 | Teutsch et al. | 514/179 |
| 4,609,651 | 9/1986 | Rohde et al. | 514/179 |
| 4,780,461 | 10/1988 | Neef et al. | 514/179 |
| 4,891,368 | 1/1990 | Chwalisz et al. | 514/179 |
| 5,088,505 | 2/1992 | Nijs | 128/830 |
| 5,089,635 | 2/1992 | Neef et al. | 549/297 |
| 5,095,129 | 3/1992 | Ottow et al. | 552/510 |
| 5,108,995 | 4/1992 | Casper | 514/170 |
| 5,256,421 | 10/1993 | Casper | 424/449 |
| 5,276,022 | 1/1994 | Casper | 514/170 |

Primary Examiner—John W. Rollins

[57] ABSTRACT

The present invention is directed to cyclophasic hormonal regimens which comprise antiprogestin and progestin for human contraception whereby progestin is administered in the alternating presence and absence of an antiprogestin in effective amounts to upregulate steroid receptor levels or is alternatively dosed with effective amounts of antiprogestin to upregulate steroid receptor levels. The present invention also provides an estrogen containing cyclophasic hormonal regimen for climacteric or menopausal hormone replacement therapy comprising the administration of an effective hormone replacement amount of estrogen in alternating doses with a combined amount of estrogen and an effective amount of antiprogestin to inhibit proliferation of endometrial tissue caused by the administration of the estrogen.

10 Claims, No Drawings

ANTIPROGESTIN CYCLOPHASIC HORMONAL REGIMEN

FIELD OF THE INVENTION

The present invention is directed to cyclophasic hormonal regimens for contraception and hormone replacement therapy. More particularly, the present invention is directed to cyclophasic hormonal regimens which comprise antiprogestin and progestin for human contraception whereby progestin is continuously administered in the alternating addition and absence of an antiprogestin in effective amounts to upregulate steroid receptor levels or progestin is administered in alternating doses with effective amounts of antiprogestin to upregulate steroid receptor levels. The present invention also provides an estrogen containing cyclophasic hormonal regimen for climacteric or menopausal hormone replacement therapy comprising the administration of an effective hormone replacement amount of estrogen in alternating doses with a combined amount of estrogen and an effective amount of antiprogestin to inhibit proliferation of endometrial tissue caused by the administration of the estrogen.

BACKGROUND OF THE INVENTION

The concept of cyclophasic hormonal regimens comprising estrogens and progestins is disclosed by Robert Casper in U.S. Pat. Nos. 5,108,995; 5,256,421; and 5,276,022. The disclosures of these three U.S. Patents are hereby incorporated herein by reference.

The primary aim of both the oral contraception (OC) hormone replacement therapy (HRT) and cyclophasic regimens disclosed by Casper is to induce higher levels of progestin and estrogen receptors by an estrogen-induced increase in receptor production. The greater concentration of steroid receptors increases the sensitivity of the target organs to progestin and estrogen and allows the use of lower doses of exogenous steroids. The cyclophasic regimens of Casper upregulate the estrogen and progestin receptors in an estrogen-dominant phase of 2–4 days and then down-regulate the same receptors in a progestin-dominant phase in the next 2–4 days. In contrast to conventional oral contraception regimens which are continuously progestin-dominant, the levels of the estrogen and progestin receptors are continuously down-regulated. In both phases of the cyclophasic regimen, the estrogen dose is constant while the progestin dose is varied to produce relatively progestin-dominant or estrogen-dominant effects. These alternating phases continue without interruption for HRT but with OC, they are interrupted periodically for 4–7 days to allow menstrual bleeding to occur.

Norethindrone may be used in trials of cyclophasic phasic regimens and has a relatively short half-life. In pharmacokinetic models for contraceptive cyclophasic regimens longer half-lives for some progestin (e.g., norgestimate) given in the progestin-dominant phase is observed to cause higher than intended progestin levels to extend into the estrogen-dominant phase. This effect may indicate that a sufficiently estrogen-dominant phase is not achieved and the steroid receptors are not adequately upregulated. Without adequate upregulation, the steroid doses administered in a cyclophasic regimen are too low to maintain endometrial integrity and breakthrough bleeding rates higher than those resulting from administration of standard dose oral contraceptives have been observed in clinical trials.

An antiprogestin added to all or part of the estrogen-dominant phase of a cyclophasic regimen acts more quickly to increase the receptor levels in the estrogen-dominant phase. The mechanisms of action for this effect may be two-fold. An antiprogestin directly antagonizes the progestin receptor-binding of a progestin and prevents receptor down-regulation by the progestin. In the absence of exogenous progestin and estrogen, antiprogestins have been shown to upregulate progestin and estrogen receptors in human endometrial tissue. Following physiologic estrogen replacement in ovarectonized monkeys, antiprogestin treatment (e.g. using an antiprogestin known as RU486) induces dramatic dose-dependent rise in estradiol receptor concentrations. Despite the rise in estrogen receptor levels, an antiprogestin (RU486) inhibited endometrial proliferation and secretory activity. See Wolf et al. *Fertility and Sterility*, Vol 52. No. 6 December 1989 pp 1055–1060 and Neulen et al. *J. Clinical Endocrinology and Metabolism*, Vol. 71 No. 4, 1990 pp. 1074–1075. Low doses of an antiprogestin (10–50 mg RU486) administered in continuous or intermittent periods during the menstrual cycle inhibit ovulation. See Spitz et al. *Fertility and Sterility*, Vol. 59, No. 5, pp. 971–975.

It is therefore an object of the present invention to provide a cyclophasic hormonal regimen comprising the administration of antiprogestin which overcomes problems of breakthrough bleeding and/or excessive endometrial mitotic activity resulting in endometrial hyperplasia. It is an additional object of the present invention to progress beyond the prior art and provide novel cyclophasic regimens utilizing antiprogestin compounds for contraception and hormone replacement therapy. Additional objects and advantages of the invention will be set forth, in part in the description which follows and in part will be obvious from the description, or may be learned by practice of the invention. The objects and advantages of the invention are realized and obtained by means of the devices, combinations, and methods particularly pointed out in the appended claims.

SUMMARY OF THE INVENTION

To achieve the objects and purposes of the invention, as embodied and fully described herein the present invention provides a progestin and antiprogestin cyclophasic hormonal method and drug regimen for human contraception comprising the steps of: (a) administering an effective ovulation suppressing amount of a progestin in single daily doses for a period of 2–4 days; (b) administering an effective amount of an antiprogestin to upregulate steroid receptor levels in single daily doses for a period of the next 2–4 days; and (c) repeating the steps (a) and (b) for a total of 20–24 days. In preferred embodiments the method and regimen of the present invention comprises the additional steps of (d) administering no drug or a placebo for 4–8 days after the 20–24 days of drug administration; and (e) repeating steps (a–d).

In other embodiments of the invention a progestin, estrogen and antiprogestin cyclophasic hormonal method and drug regimen for human contraception is provided comprising the steps of: (a) administering an effective ovulation suppressing amount of a progestin and an effective breakthrough bleeding preventative amount of estrogen in a single daily dose for a period of 2–4 days; (b) administering a reduced amount of progestin and estrogen and an effective amount of an antiprogestin to upregulate steroid receptor levels in a single daily dose for a period of the next 2–4 days; and (c) repeating the steps (a) and (b) for a total of 20–24 days. In preferred embodiments the method and regimen of the invention comprises the additional steps of (d) administering no drug or a placebo for 4–8 days after the 20–24 day administration of drug; and (e) repeating steps (a–d).

In other embodiments, the present invention is directed to an estrogen containing cyclophasic hormonal method and regimen for climacteric or menopausal hormone replacement therapy comprising the steps of: (a) administering an effective hormone replacement amount of estrogen in single daily doses for a period of 2–4 days; (b) administering the same or a reduced amount of estrogen in combination with an effective amount of antiprogestin to inhibit proliferation of endometrial tissue caused by the administration of estrogen; and (c) repeating steps (a) and (b).

In further embodiments, the present invention provides a method of reducing breakthrough bleeding resulting from the administration of an effective ovulation suppressing amount of a progestin in a human contraceptive regimen comprising administering the progestin for a period of 2–4 days followed by administering an effective amount of an antiprogestin to upregulate steroid receptor levels and inhibit ovulation for a period of the next 2–4 days and repeating the above cycle for a total period of 20–24 days. Preferably, no drug or placebo is administered for the next 4–8 days after the 20–24 day and the regimen is repeated.

DETAILED DESCRIPTION OF PREFERRED EMBODIMENTS OF THE INVENTION

Reference will now be made in detail to preferred embodiments of the invention. Examples of the preferred embodiments are illustrated in the following Examples section.

Particularly preferred estrogen compositions in accordance with the invention are those which comprise substantially natural human estrogens which metabolize to estradiol and estrone sulfate, particularly preferred is estropipate. Estropipate is a piperazine salt which provides a stable source of estrone sulfate.

The progestin compounds useful in accordance with the invention are preferably selected from the group consisting of 19-nortestosterones, particularly preferred is norethindrone. The dosing of these compositions vary with the days of administration as further described below.

Antiprogestin compounds useful in accordance with the invention can be any progestin receptor antagonist or a pharmaceutically suitable agent that counteracts the normal biological activity of progestin (progesterone). A preferred antiprogestin is a progesterone receptor antagonist, for example, mifepristone, onapristone and lilopristone are particularly suitable in the practice of this invention.

Examples of antiprogestins which can be employed in this invention are RU 486 ("mifepristone", Roussel Uclaf, Paris; U.S. Pat. No. 4,386,085); and "onapristone" (Schering AG, Berlin; U.S. Pat. No. 4,780,461) and the steroids described in the following patents and patent applications: U.S. Pat. No. 4,609,651, especially the compound lilopristone (11β-(4-dimethylaminophenyl)-17β-hydroxy-17a-(3-hydroxy-prop-1-(Z)-enzyl-4,9(10) estradien3-one); U.S. Pat. No. 5,089,635, especially the compounds 11β-(4-acetylphenyl)-17β-hydroxy-17α-(1-propinyl)-4,9-estradien-3-one and 11β-(4-acetylphenyl)-17β-hydroxy-17α-(3-hydroxy-1(2)-propenyl)-4,9-estradien-3-one; U.S. Pat. No. 5,095,129; published European patent application EP-A 04042831; and other known antiprogestins, e.g. those disclosed in U.S. Pat. No. 4,891,368.

In preferred embodiments of the invention, the cyclophasic combination compositions are given in continuous regimens throughout the cycle and augmented by a placebo on a continuous daily basis. Such a daily continuous regimen has been found to be efficacious and is believed to aid in patient compliance whereby a patient gets into a daily routine of taking the prescribed medication without any distracting starting and stopping periods.

The purpose and desired effect of estrogen and progestin in each of contraception and HRT is well known to those skilled in the art and thus a dosage for estrogen and progestin, given the circumstance of co-administration with an antiprogestin as described herein, may be easily established by the skilled practitioner. In the case of contraception, estrogen should be administered in an effective amount to prevent breakthrough bleeding and progestin likewise should be administered in an effect amount to suppress ovulation. In the case of HRT, estrogen should be administered in sufficient amounts to prevent hot flashes, reduce bone loss and reduce the risk of ischemic heart disease and progestin likewise should be administered in sufficient amounts to protect the endometrium from the stimulatory effects of estrogen. Preferred exemplative dosages in accordance with the invention include but are not limited to the following daily doses: progestin in the range of 10 to 2500 mcg, more preferably about 30 to 180 mcg for norgestimate and 350 to 1500 mcg for norethindrone; antiprogestin in the range of 1 to 100 mg; and estrogen as estradiol in the range of 0.5 to 3.0 mg for hormone replacement therapy and as ethinyl estradiol in the range of 0–50 mcg for contraceptive applications.

The above described dosages are generally preferred in accordance with the invention but may be varied depending upon the results of specific clinical testing, requirements of the patient, the weight and age of the patient, relative effective potency of the drug, severity of the condition being treated in light of the patients response to the drug and the particular compound or hormone combination composition being employed. The determination of optimum dosages for a particular situation is within the skill of the medical arts.

The estrogen, antiprogestin and progestin compositions can be administered by way of any art recognized means as practiced in the pharmaceutical arts. For example, the estrogen and progestin alone or in combination may be so formulated so that it can be administered orally, via a skin patch for transdermal absorption, by intramuscular injection, contained within an inert matrix which is implanted within the body and in a depot state, or intravaginally in a matrix that slowly releases the active compositions (such implants are taught for example in U.S. Pat. Nos. 4,957,119 and 5,088,505).

Pharmaceutical compositions containing compounds of the invention may further comprise pharmaceutically acceptable carriers and be in either solid or liquid form. Solid form preparations include powders, tablets, dispersible granules, capsules, etc. The carrier may also be one or more substances which act as diluents, flavoring agents, solubilizers, lubricants, suspending agents, binders, or tablet disintegrating agents as well as encapsulating materials. Suitable carriers are magnesium carbonate, magnesium stearate, talc, lactose, sugar, peptin, dextrin, starch, methylcellulose, sodium carboxylmethylcellulose, and the like. Liquid form preparations include solutions which are suitable for oral or parenteral administration, or suspensions and emulsions suitable for oral administration.

Sterile water solutions of the active component or sterile solutions of the active components in solvents comprising water, ethanol, or propylene glycol are examples of liquid preparations suitable for parenteral administration. Aqueous solutions for oral administration can be prepared by dissolving the active compound in water and adding suitable flavorants, coloring agents, stabilizers and thickening agents as required. Aqueous suspensions for oral use can be made by dispersing the active component in water together with a viscous material such as a natural or synthetic gum, methylcellulose, sodium carboxymethyl- cellulose, and other suspending agents known to the pharmaceutical formulation art. Other solid dosage forms include topical dosage forms which include solutions, powders, fluid emulsions, fluid suspensions, semi-solids, ointments, pastes, creams, gels or jellies and foams; and parenteral dosage forms which include solutions, suspensions, emulsions or dry powder comprising an effective amount of estrogen and progestin as taught in this invention.

Various conventional techniques for preparing pharmaceutical compositions including solutions, suspensions, tablets or caplets can be employed, as would be known to those skilled in the art and as is disclosed for example by *Remington's Pharmaceutical Sciences*, Mack Publishing Co., Part 8, Chapters 76–93, Pharmaceutical Preparations and Their Manufacture, pp. 1409–1677 (1985).

The pharmaceutical formulations may be provided in kit form containing preferably about 24–30, more preferably about 28 dosage form units, e.g. caplets or tablets, intended for ingestion on successive days of an administration cycle. Where administration of the estrogen, progestin, and antiprogestin is intended to be periodically alternating, a plurality of caplets or tablets may be provided whereby a portion contains estrogen only and the remaining tablets additionally contain progestin and antiprogestin or as is otherwise desired in accordance with the method and regimen of the invention for OC and HRT applications.

It is especially advantageous to formulate the aforementioned pharmaceutical compositions in unit dosage form for ease of administration and uniformity of dosage. The term "unit dosage form" as used herein refers to physically discrete units suitable as unit dosages, each unit containing a predetermined quantity of active ingredient calculated to produce the desired therapeutic effect in association with the required pharmaceutical carrier. The term "doses" as used herein broadly encompasses the term unit dosage form or dosage units as well as continuous dosing of compositions by depot or other methods.

The dosages, however, may be varied depending upon the results of specific clinical testing, the requirements of the patient, the weight and age of the patient, the severity of the condition being treated, and the compound being employed. Determination of optimum dosages for a particular situation is within the skill of the art.

The invention will now be illustrated by an exemplary study involving the method of the invention. The examples are not intended to be limiting of the scope of the present invention but read in conjunction with the detailed and general description above, provide further understanding of the invention and outline a protocol for carrying out the methods of the invention for contraception in women of child bearing age or for HRT in climacteric, perimenopausal and postmenopausal women.

EXAMPLES

The following ingredients, procedures and medical testing are generally known and available to those skilled in the pharmaceutical and medical arts.

a. Study Description

The study is a randomized, controlled, double-blind, study of six contraceptive regimens and a standard oral contraceptive comparator. The subjects complete a one month baseline cycle with no hormonal contraceptive to document ovulation occurred. The subjects then complete three months of the assigned oral contraceptive regimen during which indicators of ovulation, laboratory measures and menstrual bleeding patterns are assessed.

b. Materials and Supplies

Test medication are supplied as follows for the progestin, i.e. norgestimate (NGM), the estrogen, i.e. ethinyl estradiol (EE) and the antiprogestin, i.e. mifepristone or RU486 (RU):

TABLE 1

Experimental CYCLOPHASIC Regimens in Protocol for Contraception

|  | NGM mcg | EE mcg | RU mg | NGM mcg | EE mcg | RU mg | NGM mcg | EE mcg | RU mg |
| --- | --- | --- | --- | --- | --- | --- | --- | --- | --- |
|  | Example 1 | | | Example 2 | | | Example 3 | | |
| Progestin phase[1] | 180 | 20 | 0 | 180 | 20 | 0 | 180 | 20 | 0 |
| Estrogen phase[2] | 30 | 10 | 10 | 30 | 0 | 25 | 0 | 0 | 25 |
|  | Example 4 | | | Example 5 | | | | | |
| Progestin phase[1] | 180 | 0 | 0 | 180 | 0 | 0 | | | |
| Estrogen phase[2] | 30 | 0 | 25 | 0 | 0 | 25 | | | |

[1]Cycle days 1–2, 5–6, 9–10, 13–14, 17–18, 21–22
[2]Cycle days 3–4, 7–8, 11–12, 15–16, 19–20

A comparator regimen of 20 mcg EE+180 mcg NGM alternating every 2–4 days with 20 mcg EE+30 mcg NGM is included.

c. Study Population

The study population for regimens 1–5 and comparator regimen are healthy premenopausal women of childbearing age protected from pregnancy by use of barrier contraception, sterilization or abstinence.

d. Methods—Ovulation and Lipid Measurement

All clinical laboratory evaluations are standard industry tests which may be performed by a central laboratory.

e. Results

With a lower dose of EE compared to the standard cyclophasic contraceptive regimen, a lowering of estrogen-related side effects (e.g., nausea, weight gain, bloating, headaches) would result. The lower EE dose would also have changes in several laboratory measures indicating lower blood coagulability and hepatic enzyme elevation.

f. Discussion

An antiprogestin can complement (example 1) or substitute for (example 2) an estrogen during the estrogen dominant phase in a cyclophasic regimen by inducing an increase in steroid receptor concentrations as an estrogen dose. An antiprogestin may also stabilize the proliferative endometrium allowing the elimination of estrogen during the progestin-dominant phase (examples 4 and 5). An antiprogestin can also function similarly to a progestin by inhibiting ovulation and stabilizing proliferative endometrium to reduce breakthrough bleeding. Therefore, an antiprogestin can substitute for a progestin in the estrogen-dominant phase (examples 3 and 5).

Examples 6–8 a. Study Description

The study is a randomized, controlled, double-blind, study of three hormone replacement therapy (HRT) regimens and a standard cyclophasic HRT comparator. The subjects will complete six months of the assigned HRT regimen during which symptom frequency, bleeding patterns and laboratory measures will be assessed.

b. Materials and Supplies

TABLE 2

Experimental CYCLOPHASIC Regimens in Protocol for Hormone Replacement Therapy

|  | NGM mcg | EP mcg | RU mg | NGM mcg | EP mcg | RU mg | NGM mcg | EP mcg | RU mg |
|---|---|---|---|---|---|---|---|---|---|
|  | Example 6 | | | Example 7 | | | Example 8 | | |
| Progestin phase[1] | 90 | 2 | 0 | 90 | 2 | 0 | 0 | 2 | 0 |
| Estrogen phase[2] | 0 | 2 | 10 | 0 | 1 | 25 | 0 | 2 | 10 |

[1]Alternating two day intervals (i.e. days 1–2, 5–6, 9–10, 13–14, 17–18, 21–22, etc.)
[2]Alternating two day intervals (i.e. days 3–4, 7–8, 11–12, 15–16, 19–20, etc.)

A comparator regimen of 2 mg EP alternating every two days with 2 mg EP+90 mcg NGM would be included.

c. Study Population

The study population for regimens 6–8 and comparator regimen are healthy perimenopausal and postmenopausal women 40 years or older.

d. Methods—Lipid Measurement

All clinical laboratory evaluations are standard industry tests which may be performed by a central laboratory.

e. Results

Menopausal symptoms, irregular bleeding and lipid changes will be improved by the addition of an antiprogestin to a standard cyclophasic HRT regimen. The standard cyclophasic regimen doses of estrogen and progestin can be reduced and clinical benefits maintained with the addition of an antiprogestin.

f. Discussion

The addition of an antiprogestin to the cyclophasic regimen potentiates the action of the estrogen and progestin by augmenting the steroid receptor increase induced by the standard cyclophasic estrogen dose (example 6). The antiprogestin allows a reduction in the estrogen dose (example 7) without a decrease in the beneficial clinical effects. The ability of the antiprogestin to reduce endometrial mitotic activity allows the antiprogestin to substitute for the progestin in preventing endometrial hyperplasia (example 8), without having the adverse lipid effects of the progestin.

The scope of the present invention is not limited by the description, examples and suggested methods described herein and modifications can be made without departing from the spirit of the invention. For example, other estrogens and progestins may be substituted for those provided in the examples herein to achieve similar advantageous results.

Applications of the compositions, protocols and methods of the present invention can be accomplished by any pharmaceutical and/or medical methods and techniques as are presently or prospectively known to those skilled in the art. It is intended that the invention cover any modifications and variations of this invention provided that they come within the scope of the appended claims and their equivalents.

What is claimed is:

1. A progestin and antiprogestin cyclophasic hormonal method and regimen for human contraception comprising the steps of:
   a) administering an effective ovulation suppressing amount of a progestin in single daily doses for a period of 2–4 days;
   b) administering an effective amount of an antiprogestin to upregulate steroid receptor levels in single daily doses for a period of the next 2–4 days; and
   c) repeating steps a and b for a total of 20–24 days.

2. The regimen of claim 1 comprising the additional steps of
   d) administering no drug or a placebo for 4–8 days; and
   e) repeating steps a–d.

3. The method of claim 1 wherein the progestin is a 19-nortestosterone and the antiprogestin is selected from the group consisting of mifepristone, onapristone and lilopristone.

4. The method of claim 1 wherein the progestin administered is norgestimate in a dosage range of about 10–250 mcg per day or norethindrone in a dosage range of about 350–2500 mcg per day and the dosage of antiprogestin provided is from about 1 to 100 mg per day.

5. The method of claim 1 wherein the regimen comprises
   a) administering an effective ovulation suppressing amount of a progestin in single daily doses for 2 days;

b) administering an effective amount of an antiprogestin to upregulate steroid receptor levels in single daily doses for a period of the next 2 days; and c) repeating steps a and b for a total of 22 days.

6. The method of claim 5 wherein the progestin administered is norgestimate in a dosage range of about 10–250 mcg per day or norethindrone in a dosage range of about 350–2500 mcg per day and the dosage of antiprogestin provided is from about 1 to 100 mg per day.

7. A method of reducing breakthrough bleeding in a human contraceptive regime comprising the steps of:

a) the administration of an effective ovulation suppressing amount of a progestin for a period of 2–4 days;

b) administering an effective amount of an antiprogestin to upregulate steroid receptor levels and inhibit ovulation levels for a period of the next 2–4 days; and c) repeating the above cycle for a total period of 20–24 days.

8. The regime of claim 7 comprising the additional steps of:

d) administering no drug or placebo of 4–8 days; and e) repeating steps a)–d).

9. The method of claim 7 wherein the estrogen is ethinyl estradiol, the progestin is a 19-nortestosterone and the antiprogestin is selected from the group consisting of mifepristone, onapristone and lilopristone.

10. The method of claim 7 wherein the estrogen is ethinyl estradiol administered in a dosage range of about 2–30 mcg per day, the progestin administered is norgestimate in a dosage range of about 10–250 mcg per day or norethindrone in a dosage range of about 350–2500 mcg per day and the dosage of antiprogestin provided is from about 1 to 100 mg per day.

* * * * *